(12) United States Patent
Yang et al.

(10) Patent No.: US 9,943,242 B2
(45) Date of Patent: *Apr. 17, 2018

(54) CARDIAC MAPPING SYSTEM AND METHOD FOR BI-DIRECTIONAL ACTIVATION DETECTION OF ELECTROGRAMS

(71) Applicant: St. Jude Medical, Cardiology Division, Inc., St. Paul, MN (US)

(72) Inventors: Chin-Ann Yang, Richmond, CA (US); Valtino X. Afonso, Oakdale, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/361,527

(22) Filed: Nov. 28, 2016

(65) Prior Publication Data

US 2017/0071493 A1    Mar. 16, 2017

Related U.S. Application Data

(63) Continuation of application No. 14/527,026, filed on Oct. 29, 2014, now Pat. No. 9,538,929.

(Continued)

(51) Int. Cl.
*A61B 5/04* (2006.01)
*A61B 5/0452* (2006.01)
*A61B 5/00* (2006.01)

(52) U.S. Cl.
CPC ........ *A61B 5/04012* (2013.01); *A61B 5/0044* (2013.01); *A61B 5/0452* (2013.01); *A61B 2576/023* (2013.01)

(58) Field of Classification Search
CPC . A61B 5/04012; A61B 5/0044; A61B 5/0452; A61B 2576/023
See application file for complete search history.

(56) References Cited

U.S. PATENT DOCUMENTS 5,662,108 A    9/1997  Budd et al.
6,434,417 B1   8/2002  Lovett
(Continued)

FOREIGN PATENT DOCUMENTS

CA      2813586   10/2013
IL       167400   12/2011
(Continued)

OTHER PUBLICATIONS

Ciaccio, Edward J. et al., "Different characteristics of complex fractionated atrial electrograms in acute paroxysmal versus long-standing persistent atrial fibrillation", Heart Rhythm, Elsevier, US, vol. 7, No. 9, pp. 1207-1215, Sep. 1, 2010.

(Continued)

*Primary Examiner* — Rex R Holmes
(74) *Attorney, Agent, or Firm* — Armstrong Teasdale LLP

(57) ABSTRACT

In a system and computer implemented method for mapping of an anatomic structure and bi-directional activation detection of electrograms such as atrial and/or ventricular electrograms, both positive and negative deflections of an electrogram signal are analyzed over an analysis time period of the signal. At least one characteristic of the electrogram signal is determined based at least in part on analyzing both positive and negative deflections of the signal over the analysis time period. The determined at least one characteristic of the atrial electrogram signal is then associated with a generated three-dimensional model of the anatomic structure.

18 Claims, 10 Drawing Sheets

Related U.S. Application Data

(60) Provisional application No. 61/897,576, filed on Oct. 30, 2013.

(56) References Cited

U.S. PATENT DOCUMENTS

| | | | |
|---|---|---|---|
| 7,381,188 | B1 | 6/2008 | Farazi |
| 7,885,707 | B2 | 2/2011 | Hauck |
| 8,038,625 | B2 * | 10/2011 | Afonso ............ A61B 5/04012 600/424 |
| 8,229,545 | B2 | 7/2012 | Afonso |
| 8,359,092 | B2 | 1/2013 | Hayam et al. |
| 8,676,305 | B2 | 3/2014 | Hayam et al. |
| 9,538,929 | B2 * | 1/2017 | Yang ................ A61B 5/04012 |
| 2007/0208260 | A1 | 9/2007 | Afonso |
| 2008/0200962 | A1 | 8/2008 | Farazi et al. |
| 2010/0094274 | A1 | 4/2010 | Narayan et al. |
| 2012/0265086 | A1 | 10/2012 | Lux |
| 2013/0253349 | A1 | 9/2013 | Hayam et al. |

FOREIGN PATENT DOCUMENTS

| | | |
|---|---|---|
| JP | 2008229307 | 10/2008 |
| JP | 2013188439 | 9/2013 |
| WO | 0047279 A1 | 2/2000 |
| WO | 2014/058664 | 4/2014 |

OTHER PUBLICATIONS

Ganesan et al., "Bipolar Electrogram Shannon Entropy at Sites of Rotational Activation Implications for Ablation of Atrial Fibrillation", Circ Arrthythm Electrophysiol, vol. 6, No. 1, pp. 48-57, 2013. Epub Dec. 23, 2012.

Hunter et al, "Validation of a Classification System to Grade Fractionation in Atrial Fibrillation and Correlation with Automated Detection Systems", Eurospace, vol. 11, No. 12, pp. 1587-1596, Dec. 2009.

Lin et al, "Novel Assessment of Temporal Variation in Fractionated Electrograms Using Histogram Analysis of Local Fractionated Interval in Patients with Persistent Atrial Fibrillation", Circ Arrhythm Electrophysiol, vol. 5, No. 5, pp. 949-956, Oct. 2012.

Takahashi et al., "Characterization of Electrograms Associated with Termination of Chronic Atrial Fibrillation by Catheter Ablation", J Am Coll Cardiol, vol. 51. No. 10, pp. 1003-1010, Mar. 11, 2008.

Verma et al., "Selective CFAE Targeting for Atrial Fibrillation Study (SELECT AF): a Multicenter, Randomized Trial", Circ Arrhythm Electrophysiol, vol. 7, pp. 55-62, Epub Jan. 14, 2014.

Barber, C. Bradford et al., "The quickhull algorithm for convex hulls", ACM trans. on mathematical software, 22(4), Dec. 1996.

* cited by examiner

CARDIAC MAPPING SYSTEM AND METHOD FOR BI-DIRECTIONAL ACTIVATION DETECTION OF ELECTROGRAMS

This application is a continuation of U.S. application Ser. No. 14/527,026, filed 29 Oct. 2014 (the '026 application), now U.S. Pat. No. 9,538,929, which claims priority to U.S. application No. 61/897,576, filed 30 Oct. 2013 (the '576 application). The '026 application and '576 application are each hereby incorporated by reference as though fully set forth herein.

BACKGROUND OF THE DISCLOSURE

A. Field of the Disclosure

The present disclosure relates generally to an electrophysiology system and method used to measure electrical activity occurring in the heart of a patient and to visualize the electrical activity and/or information related to the electrical activity. More particularly, the present disclosure relates to processing of data from complex fractionated electrograms and the use of such data in three-dimensional mapping of the electrical activity associated with complex fractionated electrograms.

B. Background Art

The heart contains two specialized types of cardiac muscle cells. The majority, around ninety-nine percent, of the cardiac muscle cells is contractile cells, which are responsible for the mechanical work of pumping the heart. Autorhythmic cells comprise the second type of cardiac muscle cells, which function as part of the autonomic nervous system to initiate and conduct action potentials responsible for the contraction of the contractile cells. The cardiac muscle displays a pacemaker activity, in which membranes of cardiac muscle cells slowly depolarize between action potentials until a threshold is reached, at which time the membranes fire or produce an action potential. This contrasts with a nerve or skeletal muscle cell, which displays a membrane that remains at a constant resting potential unless stimulated. The action potentials, generated by the autorhythmic cardiac muscle cells, spread throughout the heart triggering rhythmic beating without any nervous stimulation.

The specialized autorhythmic cells of cardiac muscle comprising the conduction system serve two main functions. First, they generate periodic impulses that cause rhythmical contraction of the heart muscle. Second, they conduct the periodic impulses rapidly throughout the heart. When this system works properly, the atria contract about one sixth of a second ahead of ventricular contraction. This allows extra filling of the ventricles before they pump the blood through the lungs and vasculature. The system also allows all portions of the ventricles to contract almost simultaneously. This is essential for effective pressure generation in the ventricular chambers. The rates at which these autorhythmical cells generate action potentials differ due to differences in their rates of slow depolarization to threshold in order to assure the rhythmical beating of the heart.

Normal autorhythmic cardiac function may be altered by neural activation. The medulla, located in the brainstem above the spinal cord, receives sensory input from different systemic and central receptors (e.g., baroreceptors and chemoreceptors) as well as signals from other brain regions (e.g., the hypothalamus). Autonomic outflow from the brainstem is divided principally into sympathetic and parasympathetic (vagal) branches. Efferent fibers of these autonomic nerves travel to the heart and blood vessels where they modulate the activity of these target organs. The heart is innervated by sympathetic and vagal fibers. Sympathetic efferent nerves are present throughout the atria (especially in the sinoatrial node) and ventricles, including the conduction system of the heart. The right vagus nerve primarily innervates the sinoatrial node, whereas the left vagus nerve innervates the atrial-ventricular node; however, there can be significant overlap in the anatomical distribution. Efferent vagal nerves also innervate atrial muscle. However, efferent vagal nerves only sparsely innervate the ventricular myocardium. Sympathetic stimulation increases heart rate and conduction velocity, whereas parasympathetic (vagal) stimulation of the heart has opposite effects.

An arrhythmia occurs when the cardiac rhythm becomes irregular, i.e., too fast (tachycardia) or too slow (bradycardia), or the frequency of the atrial and ventricular beats are different. Arrhythmias can develop from either altered impulse formation or altered impulse conduction. The former concerns changes in rhythm that are caused by changes in the pacemaker cells resulting in irregularity or by abnormal generation of action potentials by sites other than the sinoatrial node, i.e., ectopic foci. Altered impulse conduction is usually associated with complete or partial blockage of electrical conduction within the heart. Altered impulse conduction commonly results in reentry, which can lead to tachyarrhythmias. Reentry can take place within a small local region or it can occur, for example, between the atria and ventricles (global reentry). Reentry requires the presence of a unidirectional block within a conducting pathway usually caused by partial depolarization of the pacemaker cells. Arrhythmias can be either benign or more serious in nature depending on the hemodynamic consequences of arrhythmias and their potential for changing into lethal arrhythmias.

Electrophysiology studies may be used to identify and treat these arrhythmias. In one exemplary system, a measurement system introduces a modulated electric field into the heart chamber. The blood volume and the moving heart wall surface modify the applied electric field. Electrode sites within the heart chamber passively monitor the modifications to the field and a dynamic representation of the location of the interior wall of the heart is developed for display to the physician. Electrophysiology signals generated by the heart itself are also measured at electrode sites within the heart and these signals are low pass filtered and displayed along with the dynamic wall representation. This composite dynamic electrophysiology map may be displayed and used to diagnose the underlying arrhythmia.

In addition to mapping for diagnosis, the measurement system can also be used to physically locate a therapy catheter in a heart chamber. A modulated electrical field delivered to an electrode on this therapy catheter can be used to show the location of the therapy catheter within the heart. The therapy catheter location can be displayed on the dynamic electrophysiology map in real time along with the other diagnostic information. Thus the therapy catheter location can be displayed along with the intrinsic or provoked electrical activity of the heart to show the relative position of the therapy catheter tip to the electrical activity originating within the heart itself. Consequently, the physician can guide the therapy catheter to any desired location within the heart with reference to the dynamic electrophysiology map.

The dynamic electrophysiology map is generally produced in a step-wise process. First, the interior shape of the heart is determined. This information is derived from a sequence of geometric measurements related to the modulation of the applied electric field. Knowledge of the dynamic shape of the heart is used to generate a representation of the interior surface of the heart. Next, the intrinsic electrical activity of the heart is measured. The signals of physiologic origin are passively detected and processed such that the magnitude of the potentials on the wall surface may be displayed on the wall surface representation. The measured electrical activity is displayed on the wall surface representation in any of a variety of formats, for example, in various colors or shades of a color. Finally, a location current may be delivered to a therapy catheter within the same chamber. The potential sensed from this current may be processed to determine the relative or absolute location of the therapy catheter within the chamber. These various processes occur sequentially or simultaneously several hundred times a second to give a continuous image of heart activity and the location of the therapy device.

If ablation is the indicated therapy, then a therapy catheter is positioned at the desired location within the heart and energy is delivered to the therapy catheter to ablate the tissue. The use of complex fractionated atrial electrograms (CFAEs) has become one tool used to identify atrial fibrillation ablation sites. For example, in one method, utilized in the EnSite® Velocity™ mapping system available from St. Jude Medical, a set of activation events are recognized in the CFAE signal, and then time intervals between subsequent activation events are calculated. The average time interval is determined and designated as the CFE mean. Locations whose cycle length is shorter than a predetermined threshold (e.g., 120 milliseconds (ms)) are identified as potential ablation sites.

Currently used activation detection methods focus solely on negative deflections in the CFAEs. There is thus a sensitivity to catheter orientation because the direction of the waveform along the catheter can impact the directions of the deflections recorded in the CFAEs. This can also impact the average CFE determination where activation events may otherwise be defined by positive deflections. It is thus desirable for the CFAE analysis to be more robust and insensitive to catheter orientations.

BRIEF SUMMARY OF THE DISCLOSURE

In one embodiment, a computer implemented method for analyzing an electrogram signal generally comprises analyzing both positive and negative deflections of the electrogram signal over an analysis time period of the signal. At least one characteristic of the electrogram signal is determined based at least in part on analyzing both positive and negative deflections of the signal over the analysis time period.

In another embodiment, a system for mapping electrode data received from at least one electrode positionable relative to an anatomic structure to a three-dimensional model of the anatomic structure generally comprises a computing device configured to receive electrogram signals from the at least one electrode. The computing device generally comprises a processor and computer-executable instructions that, when executed by the processor, cause the computing device to a) analyze both positive and negative deflections of the electrogram signal over an analysis time period of the signal, and b) determine at least one characteristic of the electrogram signal based at least in part on analyzing both positive and negative deflections of the signal over the analysis time period.

In yet another embodiment, a computer implemented method for mapping of anatomic structure generally comprises generating a three-dimensional computer model of the anatomic structure and positioning an electrode carrier in proximity to the anatomic structure with the electrode carrier having a plurality of electrodes thereon. An electrogram signal is generated from the electrodes. At least one characteristic of the anatomic structure is determined based at least in part on positive deflections and negative deflections of the electrogram signal. The determined at least one characteristic is then associated with the three-dimensional computer model of the anatomic structure.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the drawings.

DETAILED DESCRIPTION OF THE DISCLOSURE

Figure 1:
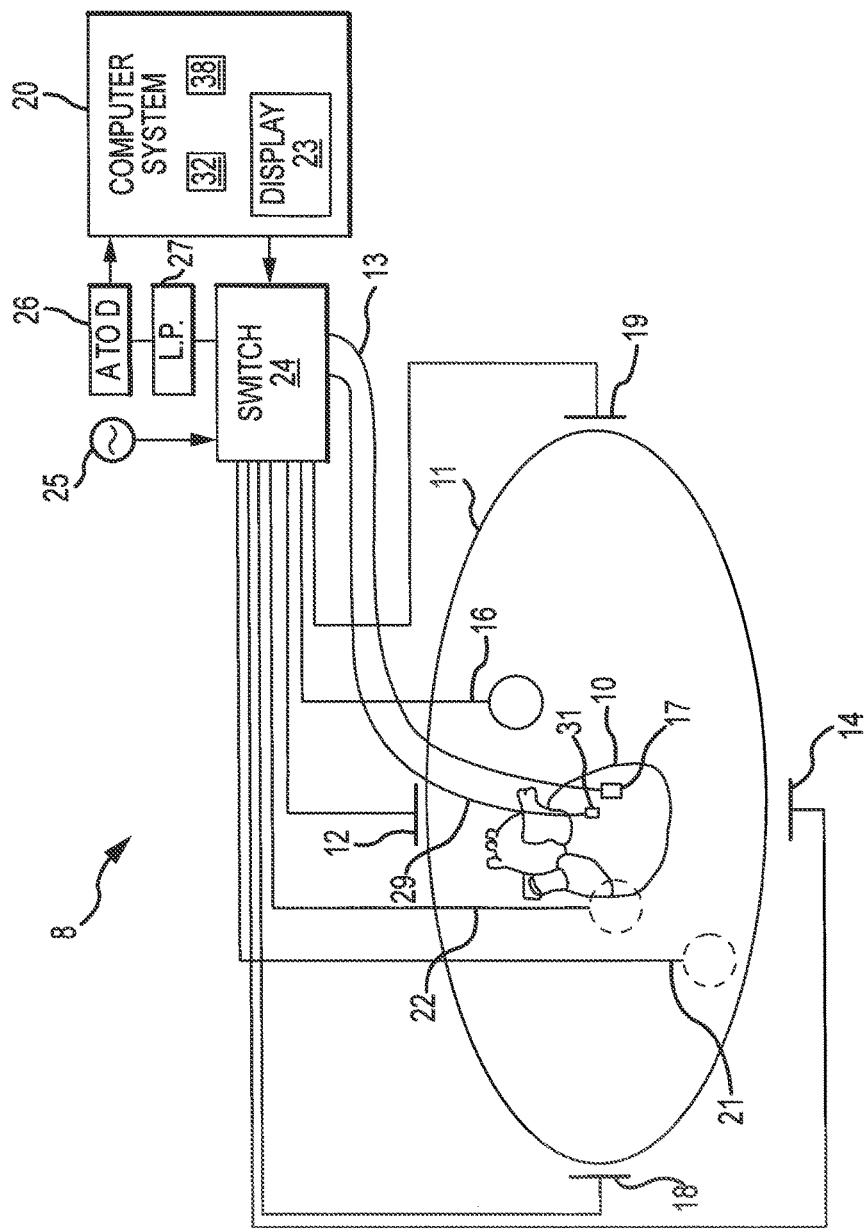
FIG. 1 is a schematic diagram of a system for performing a cardiac electrophysiology examination or ablation procedure wherein the location of one or more electrodes can be determined and recorded.

The present disclosure relates generally to mapping systems and methods for mapping anatomic structures, such as the human heart or portions thereof, and more particularly to the processing of data from electrograms—such as atrial and/or ventricular electrograms and more particularly to complex fractionated atrial electrograms (CFAEs) and the use of such data in the mapping system. In particular embodiments, the systems and methods of the present disclosure use bi-directional activation detection in analyzing CFAEs to provide a more robust analysis and to render the system insensitive to catheter orientation within the heart. While in the embodiments herein the systems and methods are used for activation detection in fractionated electrograms, it is contemplated that the systems and methods disclosed herein may be used for activation detection in non-fractionated electrograms as well. Additionally, while the various embodiments herein are described in connection with mapping of a patient's heart, it is understood that the present disclosure is not limited to mapping of a heart, and that mapping of other anatomic structures is considered to be within the scope of the present disclosure.

Known systems and methods exist for generating a three-dimensional model of an anatomic structure such as the heart, including systems that utilize technology such as CT scanning, MRI, ultrasound imaging, radar imaging, x-ray imaging, and fluoroscopic imaging. The output of such data may be a plurality of x-y-z data coordinates, spherical coordinates and/or other formats to provide a three-dimensional image. Such imaging technology is often useful in diagnosis as well as preparing for a patient's treatment and/or surgery. The imaging process may be performed hours or days before treatment and/or surgery, or concomitantly with the treatment and/or surgery. Some three-dimensional models utilize a segmented approach, including for example a segmented CT or MRI scan image. A segmented model indicates that a subregion of a three-dimensional image has been digitally separated from a larger three-dimensional image, e.g., an image of the right atrium separated from the rest of the heart. Other methodologies and techniques for creating a three-dimensional model of a portion of the patient may also be utilized in accordance with the present disclosure.

Data acquired from the imaging process is typically used to partition the three-dimensional model into discrete surface elements to facilitate numerical computation during subsequent mapping and reconstruction. It is understood that various computational methods may be used to partition the three-dimensional model into discrete segments, such as finite differences, Finite Element Methods (FEM) and Boundary Element Methods (BEM) such as spline BEM or linear BEM. The three-dimensional model of the anatomic structure generally includes a boundary surface defined by the discrete segments, with the boundary surface thus defining an interior (broadly, a first side) of the three-dimensional model and an exterior (broadly, a second side) of the three-dimensional model of the anatomic structure.

Figure 2:
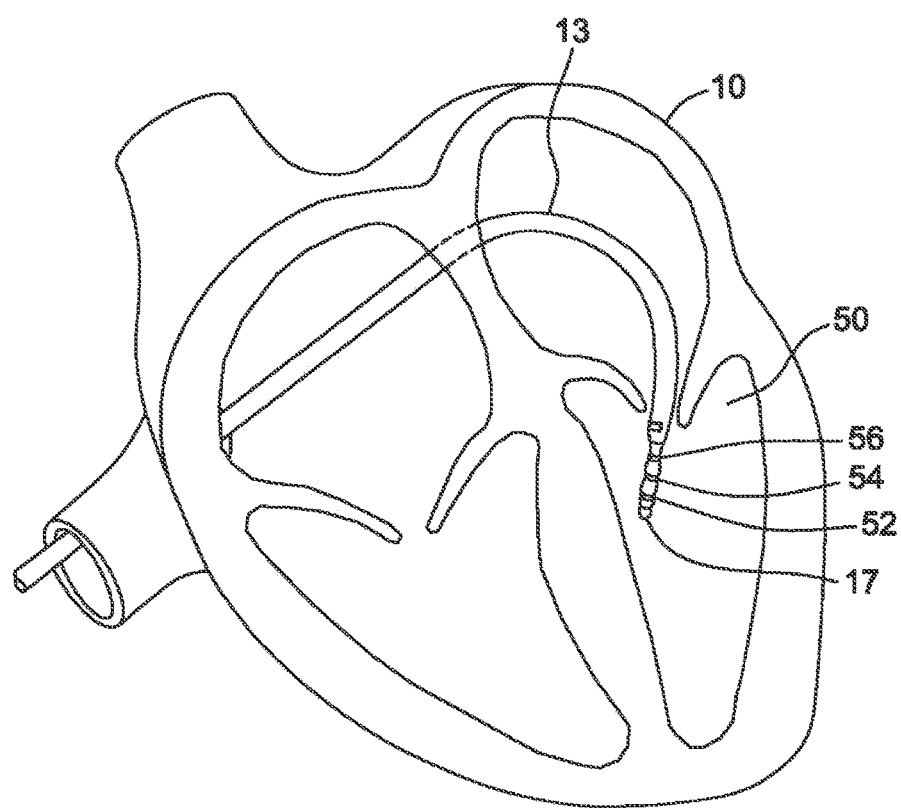
FIG. 2 is a schematic representation of a heart investigated by an electrophysiology catheter with several distal electrodes.
Figure 3:
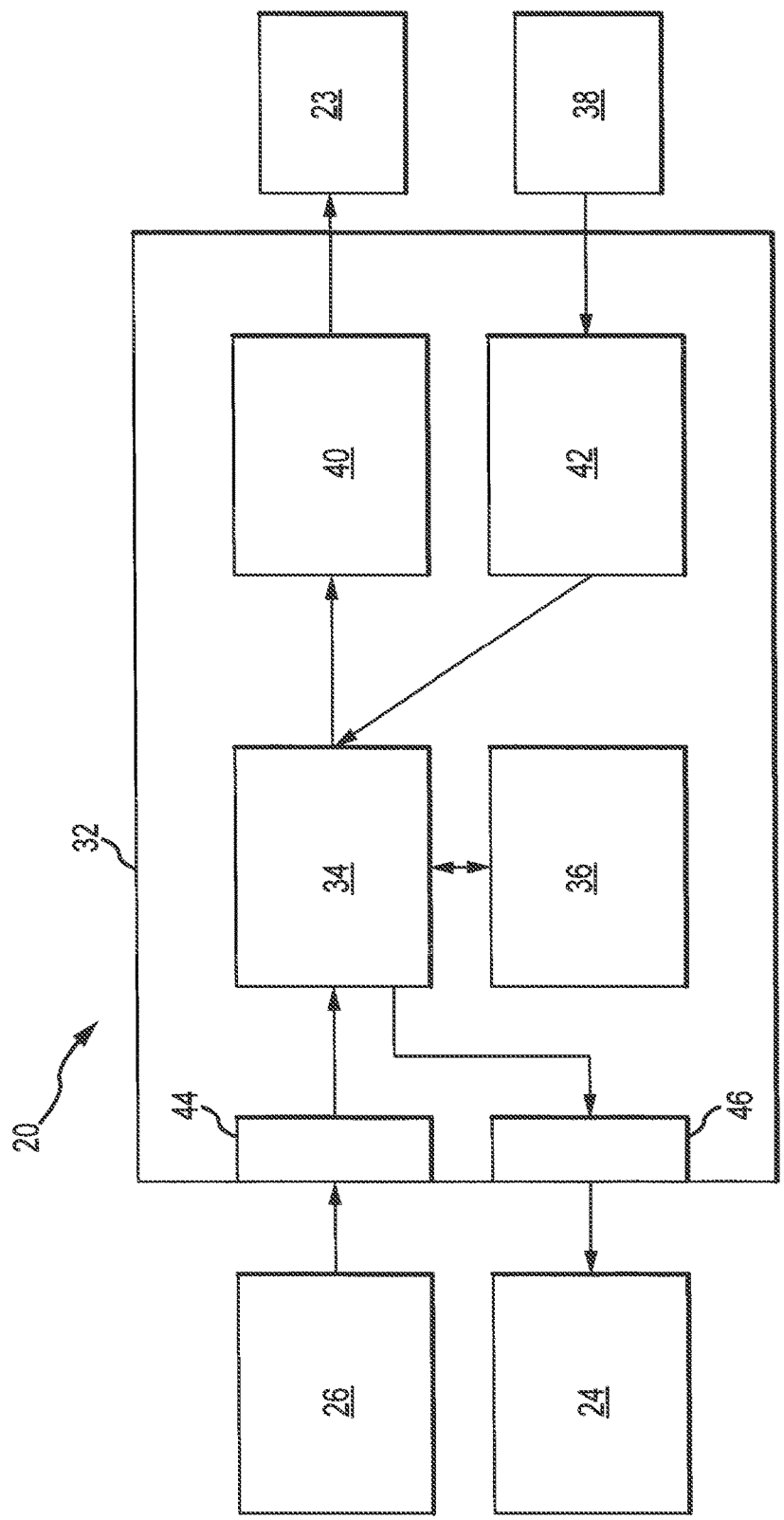
FIG. 3 is a schematic block diagram of a computing device for use in the system shown in FIG. 1.

With reference now to the drawings and in particular to FIGS. 1-3, one example of a mapping system 8 is illustrated for conducting cardiac electrophysiology studies by navigating a cardiac catheter into a heart 10 of a patient 11 to measure electrical activity occurring in the heart and to three-dimensionally map the electrical activity and/or information related to or representative of the electrical activity. The system 8 is particularly used to measure electrophysiology data at a plurality of points along an endocardial surface, and store the measured data in association with location information for each measurement point at which the electrophysiology data was measured. In one embodiment, for example, the system 8 can instantaneously locate up to sixty-four electrodes in and/or around a heart and the vasculature of a patient, measure electrical activity at up to sixty-two of those sixty-four electrodes, and provide a three-dimensional map of time domain and/or frequency domain information from the measured electrical activity (e.g., electrograms) for a single beat of the heart 10. The number of electrodes capable of being simultaneously monitored is limited only by the number of electrode lead inputs into the system 8 and the processing speed of the system 8. The electrodes may be stationary or may be moving. In addition, the electrodes may be in direct contact with the wall of the heart, or may be merely generally adjacent to the wall of the heart, to collect the electrical activity. In another embodiment, an array of electrodes is used for collecting electrical activity at multiple locations along the wall of the heart. Such an array electrode is described in detail in U.S. Pat. No. 5,662,108, which is hereby incorporated by reference herein in its entirety.

In one suitable embodiment, the localization/mapping system 8 may be the EnSite™ Velocity™ navigation and visualization system available from St. Jude Medical, Inc. In other embodiments, any other suitable localization/mapping system may be used.

The patient 11 is depicted schematically as an oval for simplicity. Three sets of surface electrodes (e.g., patch electrodes) are shown applied to a surface of the patient 11 along an X-axis, a Y-axis, and a Z-axis. The X-axis surface electrodes 12, 14 are applied to the patient along a first axis, such as on the lateral sides of the thorax region of the patient (e.g., applied to the patient's skin underneath each arm) and may be referred to as the Left and Right electrodes. The Y-axis electrodes 18, 19 are applied to the patient along a second axis generally orthogonal to the X-axis, such as along the inner thigh and neck regions of the patient, and may be referred to as the Left Leg and Neck electrodes. The Z-axis electrodes 16, 22 are applied along a third axis generally orthogonal to the X-axis and the Y-axis, such as along the sternum and spine of the patient in the thorax region and may be referred to as the Chest and Back electrodes. The heart 10 lies between these pairs of surface electrodes. An additional surface reference electrode (e.g., a "belly patch") 21 provides a reference and/or ground electrode for the system 8. The belly patch electrode 21 is an alternative to a fixed intra-cardiac electrode 31. It should also be appreciated that in addition, the patient 11 will have most or all of the conventional electrocardiogram (ECG) system leads in place. This ECG information is available to the system 8 although not illustrated in the FIG. 1.

A representative catheter 13 having at least a single electrode 17 (e.g., a distal electrode) is also shown. This representative catheter electrode 17 is referred to as the "roving electrode" or "measurement electrode" throughout the specification. Typically, multiple electrodes on the catheter will be used. In one embodiment, for example, the system 8 may comprise up to sixty-four electrodes on up to twelve catheters disposed within the heart and/or vasculature of the patient. Of course, this embodiment is merely exemplary, and any number of electrodes and catheters may be used within the scope of the present invention.

The fixed reference electrode 31 (e.g., attached to a wall of the heart 10) is shown on a second catheter 29. For calibration purposes, this electrode 31 may be stationary (e.g., attached to or near the wall of the heart) or disposed in a fixed spatial relationship with the roving electrode 17. The fixed reference electrode 31 may be used in addition to or alternatively to, the surface reference electrode 21 described above. In many instances, a coronary sinus electrode or other fixed electrode in the heart 10 can be used as a reference for measuring voltages and displacements.

Each surface electrode is coupled to the multiplex switch 24, and the pairs of electrodes are selected by software running on a computer 20, which couples the electrodes to a signal generator 25. The computer 20, for example, may comprise a conventional general-purpose computer, a special-purpose computer, a distributed computer, or any other type of computer. The computer 20 may comprise one or more processors, such as a single central-processing unit, or a plurality of processing units, commonly referred to as a parallel processing environment.

The signal generator 25 excites a pair of electrodes, for example the Y-axis electrodes 18, 19, which generates an electric field in the body of the patient 11 and the heart 10.

During the delivery of the current pulse, the remaining surface electrodes are referenced to the surface electrode 21, and the voltages induced on these remaining electrodes are filtered via a low pass filter (LPF) 27. The LPF 27 may, for example, comprise an anti-aliasing filter (e.g., a 300 Hz analog LPF). The output of the LPF 27 is then provided to an analog-to-digital (A/D) converter 26 that converts the analog signal to a digital data signal. Further low pass filtering of the digital data signal may be subsequently performed by software executed on the computer 20 to remove electronic noise and cardiac motion artifact. This filtering may, for example, comprise a user-selectable cutoff frequency used to reduce noise. In this manner, the user can customize the system to trade off signal noise against signal fidelity according to the user's individual preferences. In this fashion, the surface electrodes are divided into driven and non-driven electrode sets. A pair of surface electrodes (e.g., the X-axis electrodes 12, 14) are driven by the signal generator 25, and the remaining, non-driven surface electrodes and other reference electrodes, if any, (e.g., the Y-axis electrodes 18, 19, the Z-axis electrodes 16, 22, the surface reference electrode 21, and, if present, the fixed reference electrode 31) are used as references to synthesize the position of any intracardial electrodes.

Generally, three nominally orthogonal electric fields are generated by a series of driven and sensed electric dipoles in order to realize catheter navigation in a biological conductor. Alternately, these orthogonal fields can be decomposed and any pairs of surface electrodes can be driven as dipoles to provide effective electrode triangulation. Additionally, such nonorthogonal methodologies add to the flexibility of the system. For any desired axis, the potentials measured across an intra-cardiac electrode 17 resulting from a predetermined set of drive (source-sink) configurations are combined algebraically to yield the same effective potential as would be obtained by simply driving a uniform current along the orthogonal axes. Thus, any two of the surface electrodes 12, 14, 16, 18, 19, 22 may be selected as a dipole source and drain with respect to a ground reference, e.g., the belly patch 21, while the unexcited electrodes measure voltage with respect to the ground reference. The measurement electrode 17 placed in the heart 10 is exposed to the field from a current pulse and its voltage is measured with respect to ground, e.g., with respect to the belly patch 21. In practice, the catheters within the heart may contain multiple electrodes, and each electrode potential may be measured. As previously noted, at least one electrode may be fixed to the interior surface of the heart to form a fixed reference electrode 31, which is also measured with respect to ground. Data sets from each of the surface electrodes, the internal electrodes, and the virtual references are all used to determine the location of the measurement electrode 17 or other electrodes within the heart 10.

All of the raw electrode voltage data is measured by the A/D converter 26 and stored by the computer 20 under the direction of software. This electrode excitation process occurs rapidly and sequentially as alternate sets of surface electrodes are selected and the remaining non-driven electrodes are used to measure voltages. This collection of voltage measurements is referred to herein as the "electrode data set." The software has access to each individual voltage measurement made at each electrode during each excitation of each pair of surface electrodes. The raw electrode data is used to determine the "base" location in three-dimensional space (X, Y, Z) of the electrodes inside the heart, such as the roving electrode 17, and any number of other electrodes located in or around the heart and/or vasculature of the patient 11. FIG. 2 shows a catheter 13, which may be a conventional electrophysiology (EP) catheter, extending into the heart 10. In FIG. 2, the catheter 13 extends into the left ventricle 50 of the heart 10. The catheter 13 comprises the distal electrode 17 discussed above with respect to FIG. 1 and has additional electrodes 52, 54, and 56. Since each of these electrodes 17, 52, 54, 56 lies within the patient (e.g., in the left ventricle 50 of the heart in this example), location data may be collected simultaneously for each of the electrodes. In addition, when the electrodes are disposed adjacent to the surface, although not necessarily directly on the surface of the heart, and when the signal source 25 is "off" (i.e., when none of the surface electrode pairs is energized), at least one of the electrodes 17, 52, 54, and 56 can be used to measure electrical activity (e.g., voltage) on the surface of the heart 10.

In summary, the system 8 first selects a set of electrodes and then drives them with current pulses. While the current pulses are being delivered, electrical activity, such as the voltages measured at least one of the remaining surface electrodes and in vivo electrodes are measured and stored. At this point, compensation for artifacts, such as respiration and/or impedance shifting may be performed as indicated above. As described above, various location data points are collected by the system 8 that are associated with multiple electrode locations (e.g., endocardial electrode locations). Each point in the set has coordinates in space. In one embodiment, the system 8 collects location data points for up to sixty-four electrodes that may be located on up to twelve catheters simultaneously or in close proximity to one another. However, smaller or larger data sets may be collected and result in less complex and lower resolution or more complex and higher resolution representations of the heart, respectively.

The electrode data may also be used to create a respiration compensation value used to improve the raw location data for the electrode locations as described in U.S. Pat. No. 7,263,397, which is hereby incorporated herein by reference in its entirety. The electrode data may also be used to compensate for changes in the impedance of the body of the patient as described, for example, in U.S. Pat. No. 7,885,707, which is also incorporated herein by reference in its entirety.

The data used to determine the location of the electrode(s) within the heart are measured while the surface electrode pairs impress an electric field on the heart. A number of electrode locations may be collected by either sampling a number (e.g., sixty-two electrodes spread among up to twelve catheters) simultaneously or in sequence (e.g., multiplexed) and/or by sampling one or more electrodes (e.g., the roving electrode 17) being moved within the patient (e.g., a chamber of the heart). In one embodiment, the location data for individual electrodes are sampled simultaneously, which allows for collection of data at a single stage or phase of a heartbeat. In another embodiment, location data may be collected either synchronously with one or more phases of the heartbeat or without regard for any particular stage of the heartbeat. Where the data is collected across the phases of the heartbeat, data corresponding to locations along the wall of the heart will vary with time. In one variation, the data corresponding to the outer or inner locations may be used to determine the position of the heart wall at the maximum and minimum volumes, respectively. For example, by selecting the most exterior points it is possible to create a "shell" representing the shape of the heart at its greatest volume.

A three-dimensional model of a portion of the patient, e.g., a region of the patient's heart or surrounding vasculature, may be created from the location data points, e.g., during the same or a previous procedure, or a previously generated three-dimensional model, e.g., a segmented CT or MRI scan image, may be used. A segmented model indicates that a subregion of a three-dimensional image has been digitally separated from a larger three-dimensional image, e.g., an image of the right atrium separated from the rest of the heart. Exemplary segmentation applications include ANALYZE (Mayo, Minneapolis, Minn.), Verismo™ (St. Jude Medical, Inc., St. Paul, Minn.), and CardEP (General Electric Medical Systems, Milwaukee, Wis.). Where the three-dimensional model is created from the location data points collected by the system 8, for example, during a single procedure, the exterior-most location points in the data can be used to determine a shape corresponding to the volume of a region of the patient's heart.

In one variation, for example, a convex hull may be generated using standard algorithms such as the Qhull algorithm. The Qhull algorithm, for example, is described in Barber, C. B., Dobkin, D. P., and Huhdanpaa, H. T., "The Quickhull algorithm for convex hulls," ACM Trans. on Mathematical Software, 22(4):469-483, December 1996. Other algorithms used to compute a convex hull shape are known and may also be suitable for use in implementing the invention. This surface is then re-sampled over a more uniform grid and interpolated to give a reasonably smooth surface stored as a three-dimensional model for presentation to the physician during the same or a later procedure. Such a three-dimensional model, for example, provides an estimated boundary of the interior of the heart region from the set of points.

FIG. 3 is a block diagram of the computer system 20. The computer system 20 includes the computing device 32, the display device 23, and the input device 38. The computing device 32 includes a display adapter 40 communicatively coupling the computing device 32 to the display device 23. Display device 23 may include, without limitation, a monitor, a television display, a plasma display, a liquid crystal display (LCD), a display based on light emitting diodes (LED), a display based on a plurality of organic light-emitting diodes (OLEDs), a display based on polymer light-emitting diodes (PLEDs), a display based on a plurality of surface-conduction electron-emitters (SEDs), a display including a projected and/or reflected image or any other suitable electronic device or display mechanism. In one embodiment, display device 23 includes a touch-screen with an associated touch-screen controller. An interface adapter 42 couples the computing device 32 to the input device 38. Computing device 32 includes an input 44 configured to receive electrode signals through A/D converter 26. An output 46 couples control signals from computing device 32 to multiplex switch 24. Input device 38 includes, without limitation, a keyboard, a keypad, a touch-sensitive screen, a mouse, a scroll wheel, a pointing device, an audio input device employing speech-recognition software, and/or any suitable device that enables a user to input data into computing device 32. In some embodiments, input device 38 and display device 23 are integrated into a single input/display device, such as in a touch screen display device.

The computing device 32 includes a processor 34 and a memory device 36 coupled to the processor 34. The term "processor" refers herein generally to any programmable system including systems and microcontrollers, reduced instruction set circuits (RISC), application specific integrated circuits (ASIC), programmable logic circuits, field programmable gate array (FPGA), gate array logic (GAL), programmable array logic (PAL), digital signal processor (DSP), and any other circuit or processor capable of executing the functions described herein. The above examples are exemplary only, and thus are not intended to limit in any way the definition and/or meaning of the term "processor." Moreover, although a single processor is illustrated in FIG. 3, the processor 34 may include more than one processor and the actions described herein may be shared by more than one processor.

The memory device 36 stores program code and instructions, executable by the processor 34. When executed by the processor 34, the program code and instructions cause the processor 34 to operate as described herein. The memory device 36 may include, but is not limited to only include, non-volatile RAM (NVRAM), magnetic RAM (MRAM), ferroelectric RAM (FeRAM), read only memory (ROM), flash memory and/or Electrically Erasable Programmable Read Only Memory (EEPROM). Any other suitable magnetic, optical and/or semiconductor memory, by itself or in combination with other forms of memory, may be included in the memory device 36. The memory device 36 may also be, or include, a detachable or removable memory, including, but not limited to, a suitable cartridge, disk, CD ROM, DVD or USB memory. Although illustrated separate from the processor 34, memory device 36 may be integrated with the processor 34.

The memory device 36 stores instructions (e.g., software code) that, when executed by the processor 34, cause the processor 34 to operate as described above and in accordance with the methods set forth herein.

Figure 4:
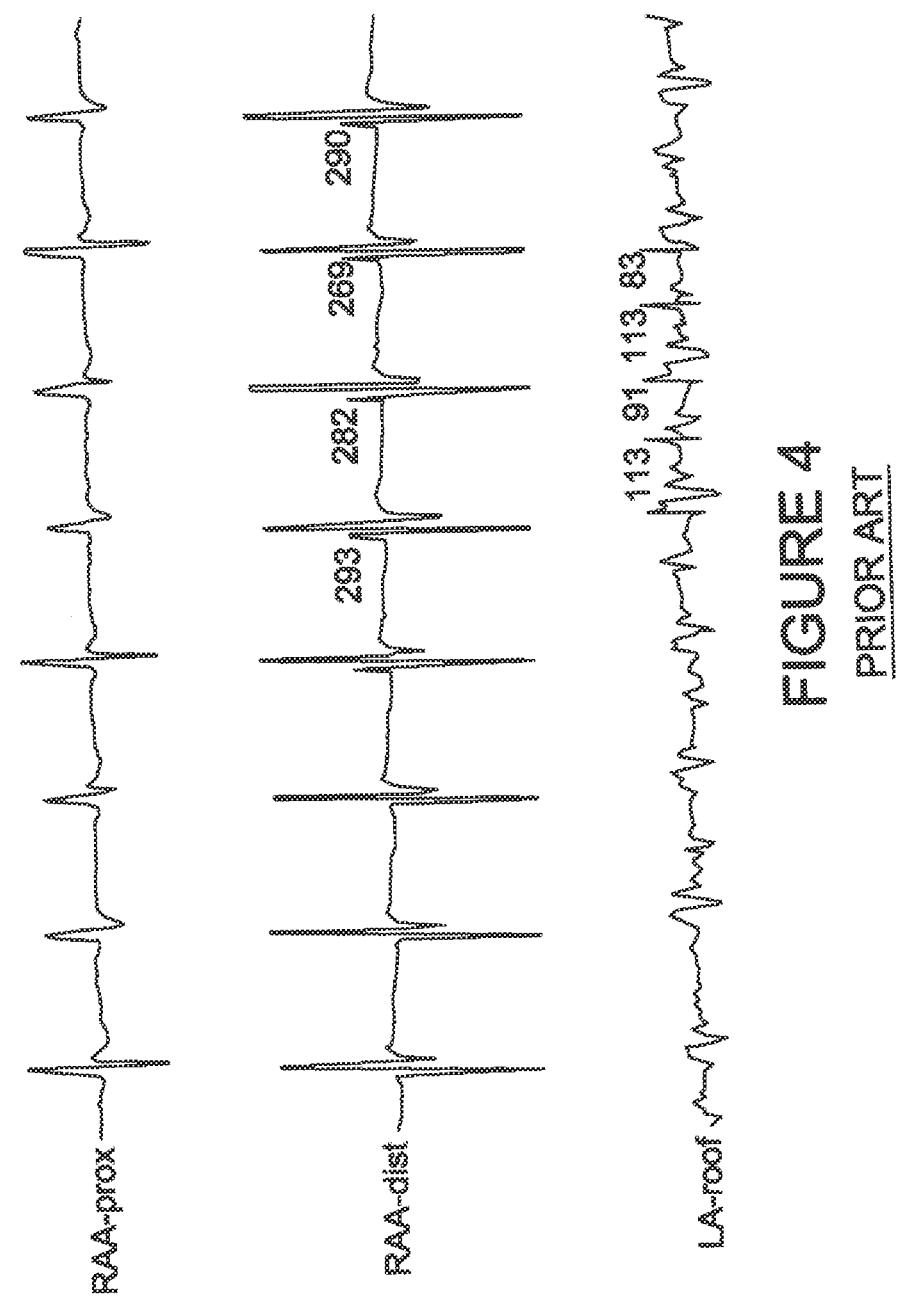
FIG. 4 illustrates examples of time-varying electrograms collected for various locations along the wall of a heart.

In one embodiment, atrial electrogram information, and in a more particular embodiment complex fractionated electrogram (CFE) information, may be mapped to the three-dimensional model. In one example, such mapping of CFE information may be useful to identifying and guiding ablation targets for atrial fibrillation. CFE information refers to irregular electrical activation (e.g., atrial fibrillation) in which an electrogram comprises at least two discrete deflections and/or perturbation of the baseline of the electrogram with continuous deflection of a prolonged activation complex (e.g., over a 10 second period). Electrograms having very fast and successive activations are, for example, consistent with myocardium having short refractory periods and micro-reentry. FIG. 4, for example, shows a series of atrial electrograms. The first two electrograms, RAA-prox and RAA-dist, comprise typical electrograms from the right atrium of a patient such as from a proximal roving electrode and a distal roving electrode in the right atrium of a patient, respectively. The third electrogram, LA-roof, comprises a CFE, such as from the roof of the patient's left atrium. In this third electrogram, LA-roof, the cycle lengths indicated by the numbers shown in the electrogram are substantially shorter than the cycle lengths indicated by the numbers shown in the first two electrograms, RAA-prox and RAA-dist.

The presence of CFE information can be detected from the electrophysiology (EP) information (e.g., electrograms) collected by an electrode. For example, time instant and/or other quantifications of the fractionation of the electrogram may be used to determine the presence and/or absence of CFE information. The mean interval between discrete activations (referred to as CFE mean) within a predetermined analysis time period of an electrogram signal may, for example, be used as an index to quantify the degree of fractionation of a given electrogram. Preferably, the mean interval between discrete activations within a predetermined analysis time period of an overall electrogram signal may be calculated for a plurality of locations within the heart, so that comparisons may be made from one location on the heart to another. This may be accomplished using a plurality of electrodes, or by using the same electrodes repositioned at a plurality of locations. Software may be used to display mean interval information as a function of location on the heart, for example, by assigning colors to various measured values. Such software provides the user of the system 8 with a visual tool to help identify potential problem areas.

While not discussed further herein, in other embodiments a standard deviation calculation may be used for the CFE information. It has been discovered that standard deviation calculations for CFE information provide a useful metric for determining the presence and/or absence of CFE information, and accordingly, is a useful metric for identifying areas that may need ablating. The presence of CFE information can be detected from the EP information (e.g., electrograms) collected by an electrode, for example, by monitoring the number of deflections within an electrogram segment and calculating the standard deviation of the time intervals between discrete activations within an electrogram segment.

It is also possible to utilize software to analyze and identify the occurrences of discrete activations, which information may then be evaluated for mean intervals and/or standard deviations. Measurements may be calculated using known algorithms on sections of data for analysis time periods of less than 1 second or for much longer time periods of several seconds, such as 20-60 seconds. In one embodiment the analysis time period suitably ranges from about 1 second to about 10 seconds, and more suitably for time periods ranging from about 3 seconds to about 8 seconds. In one embodiment, the user may specify the window for analysis. Software may be used to display mean interval (CFE mean) and/or standard deviation information as a function of location on the heart, for example, by assigning colors to various measured values on the three-dimensional mapping. Such software provides the user of the system with a visual tool to help identify potential problem areas.

Where both mean interval and standard deviation information is to be displayed, this may take the form of two separate images that may be compared to each other, or a single image in which the two sets of data are superimposed upon the same three-dimensional model. Another way to display the combined information is to mathematically relate the two metrics, for example, the standard deviation divided by the mean, or the mean divided by the standard deviation, and then display the result on a single image, again assigning colors to various calculated values. Such presentation software provides the user of the system 8 with a visual tool to help identify potential problem areas using both mean and standard deviation information. A physician, for example, may find it of significance that a particular location has a high standard deviation and a low mean.

In diagnosing atrial fibrillation and guiding an ablation catheter, the electrograms corresponding to physiological mechanisms for initiating and sustaining atrial fibrillation may be identified by quantifying the fractionation of the electrograms. These quantifications, in turn, may be used to identify regions to be ablated to eliminate the atrial fibrillation. Mid-diastolic potentials within an ischemic area of the cardiac chamber may also be identified by quantifying the fractionation of the electrograms collected in a region of the heart. Healthy tissue would correspond to non-fractionated electrograms (i.e., a single discrete activation), while unhealthy tissue (e.g., ischemic tissue) would correspond to fractionated electrograms (i.e., multiple discrete activations and/or perturbations of the baseline). The time instant or other quantifications of CFE information in electrograms may then be mapped to a three-dimensional model as described above.

Figure 5:
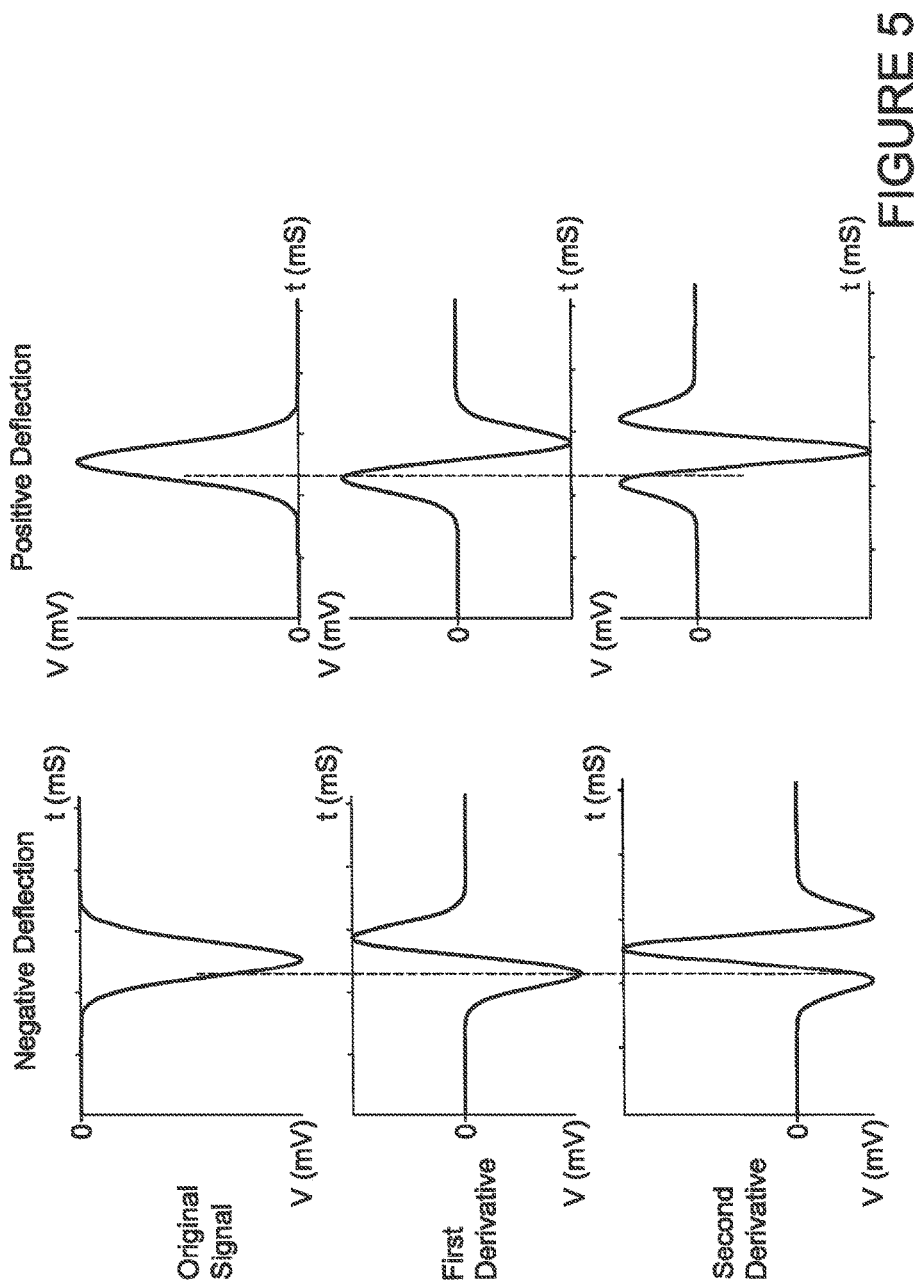
FIG. 5 is a schematic illustration of discrete time segments of a time-varying electrogram in which one time segment includes a negative deflection and the other time segment includes a positive deflection.

In analyzing the EP (electrograms) in accordance with one embodiment of the present disclosure, the processor 34 is suitably capable of bi-directional activation detection analysis that can detect both "positive" deflections (voltage going from negative to positive) and "negative" deflections (voltage going from positive to negative) on bipolar electrograms. FIG. 5 illustrates an exemplary negative deflection (left hand side) and positive deflection (right hand side) taken from respective time segments of an original electrogram signal generated over a discrete analysis time period of the original signal.

Figure 6:
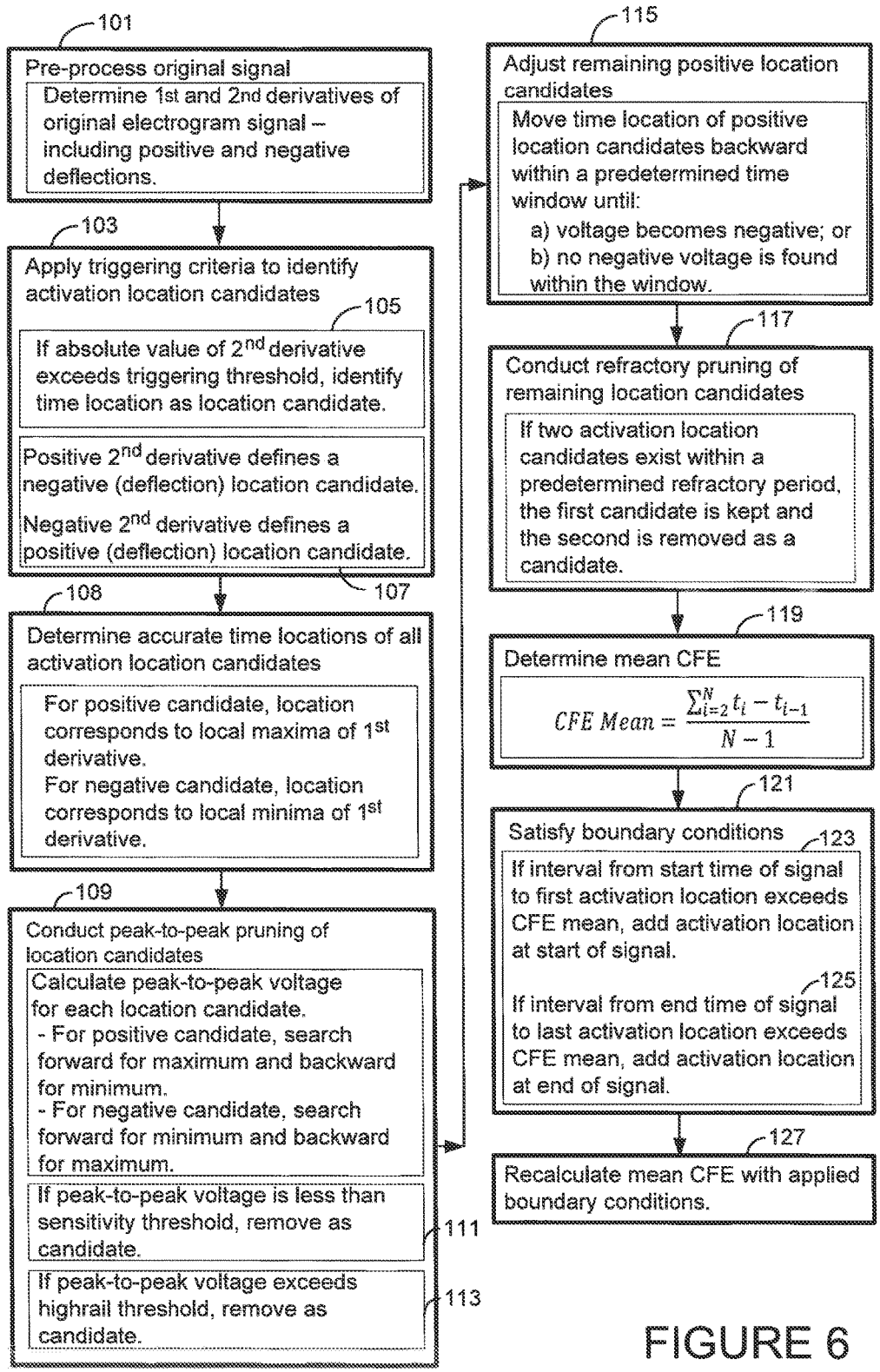
FIG. 6 is a flow diagram of one embodiment of a method for bi-directional activation detection of an atrial electrogram.

FIG. 6 is a flow diagram of one embodiment of a method for bi-directional activation detection and analysis of an electrogram such as an atrial electrogram, and more particularly in some embodiments a complex fractionated atrial electrogram. In a first step (e.g., following generation of an electrogram using the one or more catheter electrodes 17, 52, 54, 56 as described previously herein), referred to herein as a preprocessing step 101, the first and second derivatives (as illustrated in FIG. 5) are calculated for the electrogram signal over the analysis time period of the signal to determine the sharpest slope of the positive and negative deflections along the electrogram signal. In some embodiments, the first and second derivatives are calculated over 3 millisecond (ms) time intervals along the discrete time period of the signal and are defined as the difference in voltages $S(t+\Delta t)-S(t)$ over the time interval. In other embodiments, the time intervals over which the derivatives are calculated may be other than 3 ms, although increasing the time interval can result in picking up broader changes (e.g., spikes) in the original signal.

Next, with continued reference to FIG. 6, the electrogram signal is subjected to a triggering criterion step 103 in which candidates for activation detection location markers are identified over the analysis time period. In particular, at 105 if the absolute value of the second derivative is greater than a pre-determined threshold at time along the original signal, for example such as a threshold of 0.05, the time location at which this occurs along the original signal becomes a candidate for a location marker. The polarity of the location marker candidate is also determined at 107 based on the second derivative. For example, if the second derivative is positive and greater than 0.05, the time location is defined as a negative beat (e.g., a negative deflection) location marker candidate. If the second derivative, however, is negative and less than −0.05, the time location is defined as a positive beat (e.g., positive deflection) location marker candidate.

In a subsequent marker location determination step 108, accurate locations of the activation detection location marker candidates (for those identified in the triggering criterion step) are determined. In one embodiment, the locations of the markers are suitably placed on the sharpest slope on the original electrogram signal. As seen best in FIG. 5, the sharpest slope should correspond to the extrema of the first derivative. For example, the sharpest slope corresponds to a local minima of the first derivative for negative deflections, and to a local maxima of the first derivative for positive deflections.

The remaining activation detection location marker candidates are then subjected to a peak-to-peak pruning step 109. For example, in one embodiment the candidates are subjected at 111 to a peak-to-peak pruning based on voltage sensitivity—which refers to the minimum voltage difference between peaks on opposite sides (e.g., forward and backward in time) of each respective location marker candidate. If the voltage difference does not exceed a predetermined threshold—referred to as the peak-to-peak voltage sensitivity—the time location is removed as a location marker candidate. In one particularly suitable embodiment the peak-to-peak sensitivity is user definable (e.g., user input). It is contemplated that in alternative embodiments the peak-to-peak sensitivity may be pre-set upon manufacture of the system and not otherwise adjustable by the user.

To determine the peak-to-peak voltage for a given location marker candidate, the maximum and minimum voltage (of the original signal) must be determined and then the difference between these voltages is calculated. In one embodiment, this is achieved using the polarity determination made during the triggering criterion step 103 discussed above. In particular, with reference still to FIG. 5, for negative deflections a forward (in time) search is conducted on the original signal for a local minimum voltage near the location marker candidate and a backward (in time) search is conducted on the original signal for a local maximum voltage near the location marker candidate. Similarly, for positive deflections a forward (in time) search is conducted for a local maximum voltage near the location marker candidate and a backward (in time) search is conducted for a local minimum voltage near the location marker candidate. The peak-to-peak voltage is thus the difference between the local maximum voltage and the local minimum voltage. The peak-to-peak voltage is compared to the peak-to-peak sensitivity, with location marker candidates having a peak-to-peak voltage that is less than the peak-to-peak sensitivity being eliminated as location marker candidates.

In an additional or alternative peak-to-peak pruning step 113, pruning based on a peak-to-peak "highrail" (which is defined herein as a predetermined maximum peak-to-peak voltage) is conducted. The peak-to-peak voltage determined above is thus compared to the peak-to-peak highrail, with location marker candidates having a peak-to-peak voltage that exceeds the highrail being eliminated as location marker candidates. In one particularly suitable embodiment the peak-to-peak highrail is user definable (e.g., user input). It is contemplated that in alternative embodiments the peak-to-peak highrail may be pre-set upon manufacture of the system and not otherwise adjustable by the user.

Figure 7:
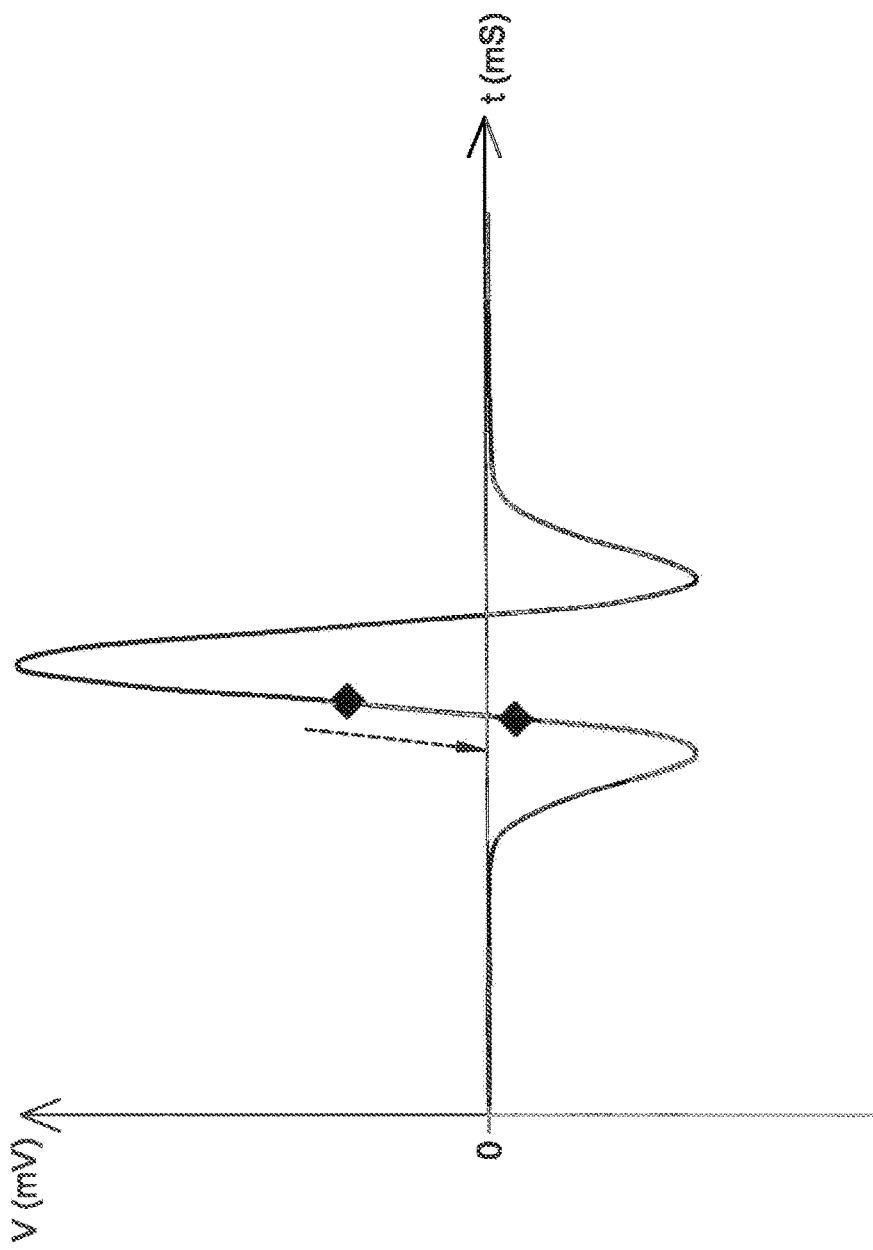
FIG. 7 is a schematic illustration of an adjustment step of the method diagrammed in FIG. 6.

In a final adjustment step 115, the locations (i.e., the time locations) of location marker candidates having a positive voltage are adjusted. In particular, for positive location marker candidates, the voltage at the sharpest slope is above 0 millivolts (mV) as illustrated in FIG. 5. In some uses of mapping systems such as mapping system 8, physicians prefer that the activation detection location markers are always placed at a time location where the voltage is negative (e.g., closer to the initiation of an activation). Accordingly, for location marker candidates that have passed previous elimination criteria and have a positive voltage, a final adjustment of the marker location is conducted to move the location marker candidates to a negative voltage, or in some instances at least a less positive voltage. For example, in one embodiment (such as illustrated in FIG. 7) the location marker candidates associated with positive voltages are moved backward (in time) until the voltage associated with the marker location is below zero, or until it searches backward in time within a determined time interval but fails to find a negative voltage.

The determined time interval according to one suitable embodiment is two times a predetermined time window (referred to herein as a CFE width). The predetermined time window (i.e., CFE width) is, according to one embodiment, a user defined time window. In other embodiments, the predetermined time window may be preset upon manufacturing and otherwise non-adjustable. In one example, the predetermined time window may be in the range of about 10 ms-20 ms. In the event that a backward (in time) search for a negative voltage results in no negative voltage being located within the determined interval (i.e., two times the predetermined time window), the location marker candidate is moved to the least positive voltage within the determined time interval. It is understood that in some embodiments this final adjustment step 115 may be omitted, such that location marker candidates may be located at a positive voltage, without departing from the scope of this invention.

In a second pruning step, the remaining activation detection location marker candidates are subjected to a refractory period pruning step 117 based on a user defined refractory period. As used herein, the refractory period refers to a time period during which, under normal heart operation, there should only be one cardiac activation. Thus, if there are more than one activation detection location marker candidates within the predetermined (and in one suitable embodiment, the user defined) refractory period, the second location marker candidate within the refractory period is eliminated. In one embodiment, a suitable refractory period may be approximately 15 ms. In other embodiments a suitable refractory period may be in the range of about 150 ms to about 200 ms. It is understood that in some embodiments the refractory period may be preset, such as upon manufacturing of the system 8 and thus otherwise not capable of selection or adjustment by the user.

Once a final set of the activation location markers is determined, boundary conditions are analyzed at 121 for purposes of determining a more purposeful CFE mean. For example, assuming a set of activation location markers at times $t_1, t_2, \ldots, t_N$ for a given time period of an electrogram signal, the CFE mean of the time period can be calculated at 119 as:

$$CFE \text{ Mean} = \frac{\sum_{i=2}^{N} t_i - t_{i-1}}{N - 1} \tag{1}$$

Figure 8:
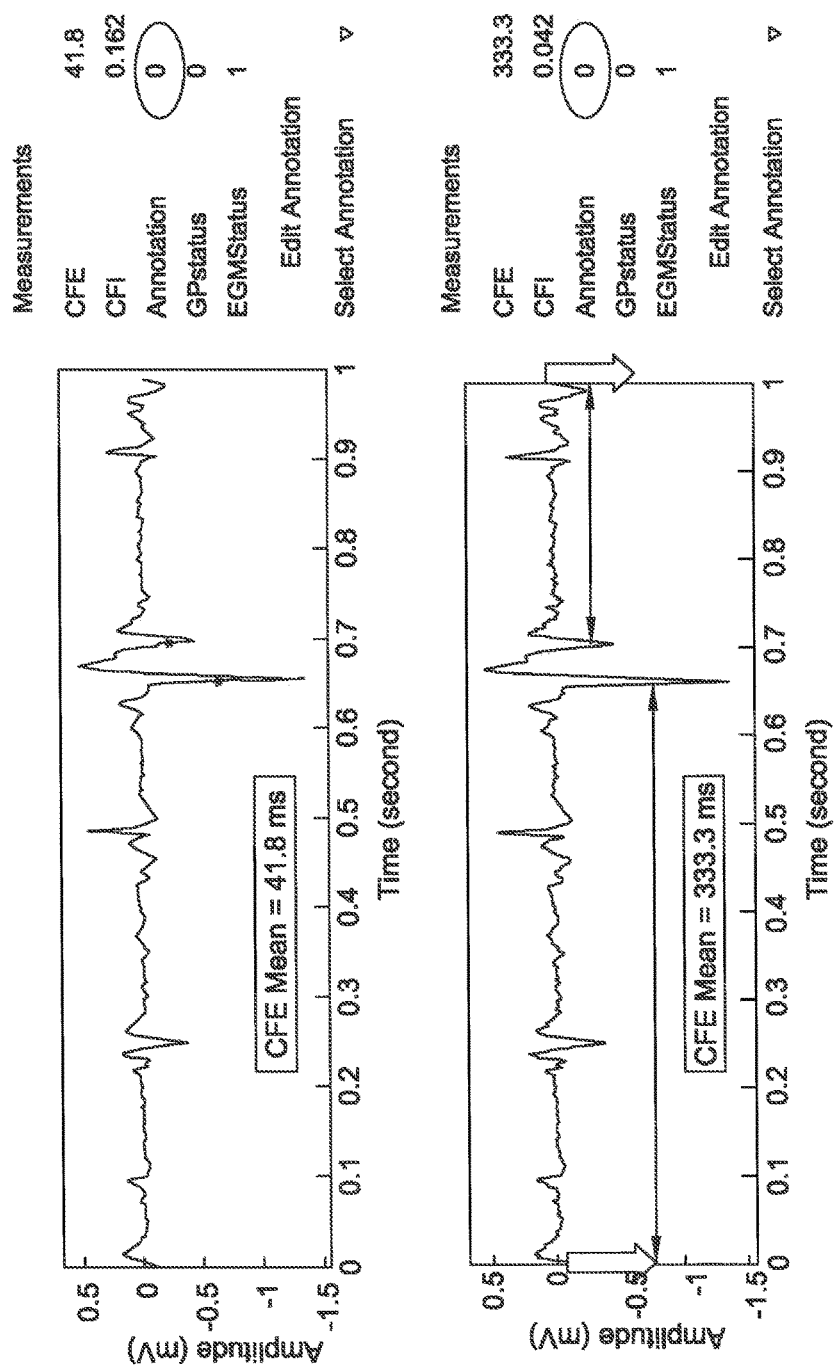
FIG. 8 is a comparison of an atrial electrogram before a boundary condition is applied in accordance with the method diagrammed in FIG. 6 and the same atrial electrogram after the boundary condition is applied.

In essence, the CFE mean calculated at 119 (e.g., without boundary conditions being satisfied) is the sum of the time intervals between successive activation location markers divided by one less than the number of location markers. FIG. 8 shows two illustrations (upper and lower) of the same analysis time period of an electrogram signal with the upper signal being subjected to the present method prior to checking the boundary conditions. Two activation location markers are identified, with the time interval therebetween (and hence the CFE mean) being 41.8 ms. The lower signal of FIG. 8 illustrates the checking and addition of boundary conditions.

To check the boundary conditions, at 123 the time interval between the start of the analysis time period and the first activation location marker (as illustrated on the lower signal of FIG. 8) is determined, and at 125 the time interval between the end of the analysis time period and the last activation location marker (as also illustrated on the lower signal of FIG. 8) is determined. The determined time intervals are each compared to the CFE mean calculated from Equation 1 at 119 to determine whether either of the time intervals is greater than the CFE mean. If so, a virtual activation location marker is added at the start and/or end of the analysis time period and the CFE mean is then recalculated at 127. For example, after applying boundary conditions to the lower signal of FIG. 9, additional activation location markers were added to the start and end of the overall analysis time period. The recalculated CFE mean is 333.3 ms.

Figure 9:
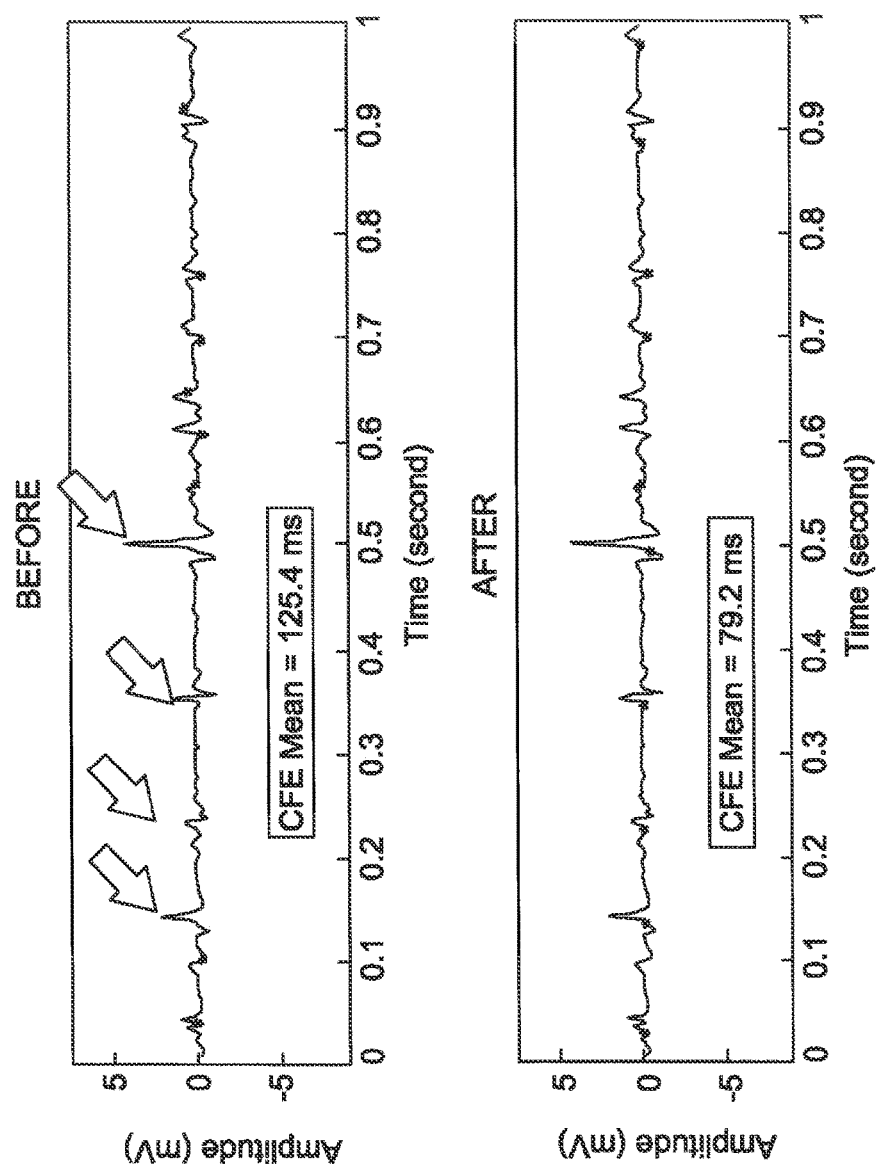
FIG. 9 is a comparison of an atrial electrogram analyzed according to a prior art method of activation detection and the same atrial electrogram analyzed in accordance with the bi-directional activation detection method diagrammed in FIG. 6.

FIG. 9 illustrates a comparison of the same electrogram signal over the same analysis time period, with the upper signal being subjected to an activation detection method that does not consider positive deflections and the lower signal being subjected to the bi-directional activation detection method described herein. As illustrated by the arrows provided on the upper signal, there are a number of cardiac activations that could be identified from positive deflections but are omitted because positive deflections are not considered. As a result, the CFE mean of the upper signal is 125.4 ms—indicating that the physical location at which the signal was generated is not a likely ablation target. When the positive deflections are taken into account according to the present method, the additional activations are detected and marked such that the resultant CFE mean is 79.1 ms—thus indicating that the physical location at which the signal was generated is of interest as a possible ablation target.

Figure 10:
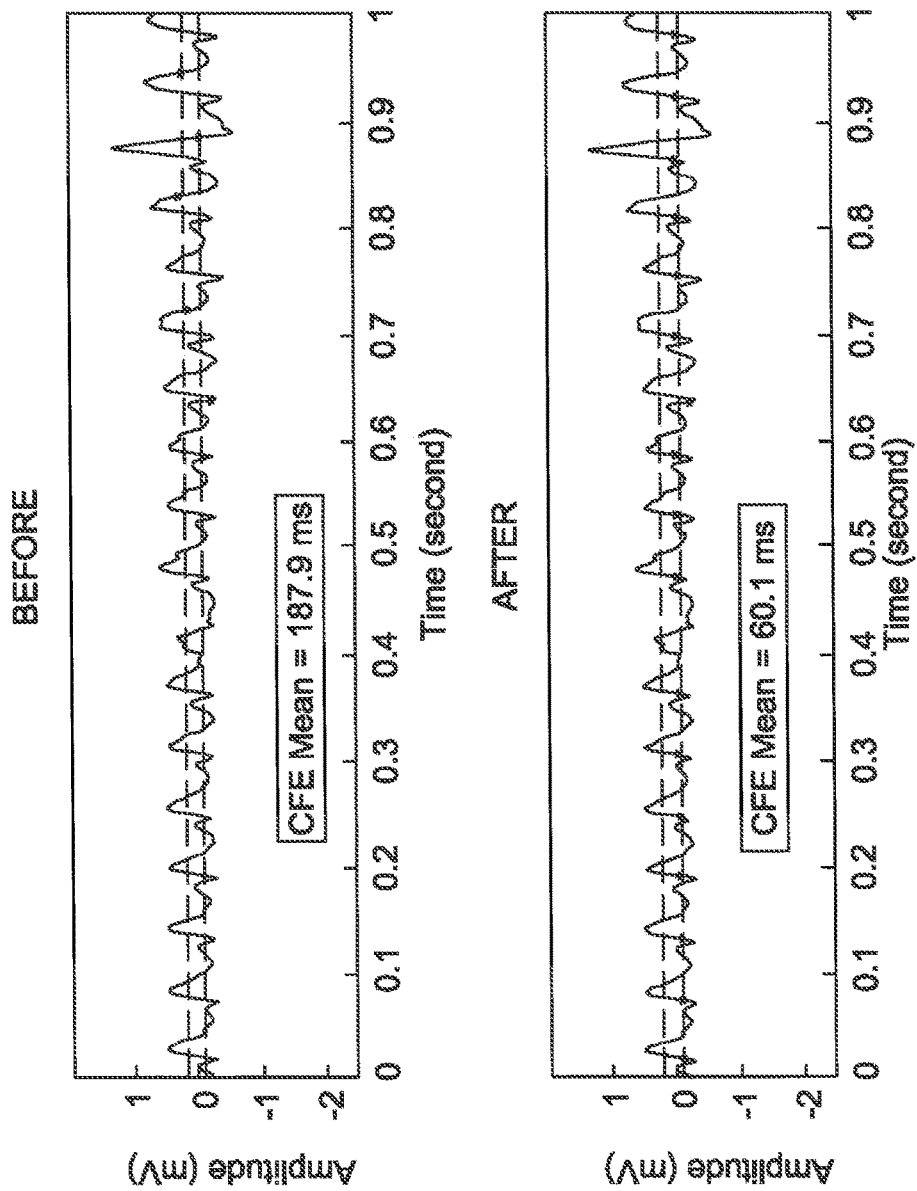
FIG. 10 is a comparison of another atrial electrogram analyzed according to a prior art method of activation detection and the same atrial electrogram analyzed in accordance with the bi-directional activation detection method diagrammed in FIG. 6.

A similar comparison, but of a different electrogram signal, is illustrated in FIG. 10, with the upper signal (analyzed according to an activation detection method that does not account for positive deflections) resulting in a calculated CFE mean of 187.9 ms. The lower signal, analyzed according to the present method to account for positive deflections, resulted in a calculated CFE mean of 60.1 ms.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the various versions, embodiment(s) or aspects thereof, the articles "a", "an", "the" and "said" are intended to mean that there are one or more of the elements. The terms "comprising", "including" and "having" are intended to be inclusive and mean that there may be additional elements other than the listed elements. The use of terms indicating a particular orientation (e.g., "top", "bottom", "side", etc.) is for convenience of description and does not require any particular orientation of the item described.

As various changes could be made in the above without departing from the scope of the disclosure, it is intended that all matter contained in the above description and shown in the accompanying drawings shall be interpreted as illustrative and not in a limiting sense.

What is claimed is:

1. A computer implemented method for analyzing an electrogram signal, the computer implemented method comprising:
   receiving, at a computing device, a complex fractionated atrial electrogram (CFAE) signal;
   analyzing both positive and negative deflections of said signal over an analysis time period of said signal;
   determining at least one characteristic of said signal based at least in part on analyzing both positive and negative deflections of said signal over said analysis time period, wherein determining at least one characteristic of said signal comprises:
      determining time locations of a plurality of cardiac activations over said analysis time period of said signal by:
         determining activation location marker candidates; and
         for each activation location marker candidate:
            determining a maximum peak and a minimum peak;
            determining a peak-to-peak voltage as a difference between the maximum peak and the minimum peak; and
            eliminating the activation location marker candidate if the peak-to-peak voltage is below a predetermined minimum peak-to-peak voltage threshold; and
      determining a complex fractionated electrogram (CFE) mean between successive time locations of the plurality of cardiac activations; and
   mapping the at least one characteristic of said signal to a three-dimensional model of an anatomic structure.

2. The computer implemented method of claim 1, wherein determining at least one characteristic of said signal further comprises:
   applying a boundary condition criteria to the determination of time locations of the plurality of cardiac activations at a beginning and end of said analysis time period of said signal; and
   recalculating the CFE mean between successive time locations of the plurality of cardiac activations following application of the boundary condition criteria.

3. The computer implemented method of claim 1, wherein the step of determining time locations of a plurality of cardiac activations comprises subjecting said signal to a processing step in which a first derivative and a second derivative are determined for the said signal over said analysis time period, and determining the time location of each cardiac activation at least in part as a function of at least one of the first derivative and the second derivative of said signal.

4. The computer implemented method of claim 3 wherein the step of determining the time location of at least one cardiac activation comprises, subsequent to the processing step, further subjecting said signal to a triggering step in which the activation location marker candidates are determined, the triggering step comprising determining the absolute value of the second derivative of said signal over said analysis time period of the signal, and comparing the second derivative to a predetermined threshold wherein each time location at which the absolute value of the second derivative of the signal is greater than the predetermined threshold is considered as an activation location marker candidate.

5. The computer implemented method of claim 4 wherein the triggering step further comprises determining based on the second derivative a polarity of said signal at each determined activation location marker candidate, wherein i) if the second derivative is positive and greater than the predetermined threshold, the activation location marker candidate is designated as a negative location marker candidate, and ii) if the second derivative is negative and has an absolute value greater than the predetermined threshold, the activation location marker candidate is designated as a positive location marker candidate.

6. The computer implemented method of claim 5, wherein:
for each respective negative location marker candidate, the maximum peak associated with the negative location marker candidate is identified by searching backward in time from the time location of the negative location marker candidate and the minimum peak associated with the negative location marker candidate is identified by searching forward in time from the time location of the negative location marker candidate, the peak-to-peak voltage being determined as the absolute value of the difference between the voltage at the maximum peak and the voltage at the minimum peak, and
for each respective positive location marker candidate, the minimum peak associated with the positive location marker candidate is identified by searching backward in time from the time location of the positive location marker candidate and the maximum peak associated with the positive location marker candidate is identified by searching forward in time from the time location of the positive location marker candidate, the peak-to-peak voltage being determined as the absolute value of the difference between the voltage at the maximum peak and the voltage at the minimum peak.

7. The computer implemented method of claim 6 wherein the step of determining the time location of at least one cardiac activation further comprises subjecting said signal to a maximum peak-to-peak pruning step in which, for each positive location marker candidate and for each negative location marker candidate, the determined peak-to-peak voltage is compared to a predetermined maximum peak-to-peak voltage threshold and, if the determined peak-to-peak voltage is greater than the maximum peak-to-peak voltage threshold, eliminating the respective time location as an activation location marker candidate.

8. The computer implemented method of claim 6 wherein the step of determining the time location of at least one cardiac activation further comprises conducting an adjustment step in which the time location associated with at least one remaining activation location marker candidate for which the voltage of said signal is positive is adjusted rearward in time such that the voltage associated with the respective at least one remaining location marker candidate is one of negative and less positive.

9. The computer implemented method of claim 6 wherein the step of determining the time location of at least one cardiac activation further comprises subjecting said signal to a refractory period pruning step, the refractory period pruning step comprising determining whether two consecutive activation location marker candidates are located within a predetermined refractory time period and, upon determining that two consecutive activation location marker candidates are located within the refractory time period, eliminating one of the activation location marker candidates located within the refractory time period.

10. The computer implemented method of claim 1 wherein the step of determining the CFE mean between successive time locations of the plurality of cardiac activations comprises starting with the first time location of a respective cardiac activation and ending with the last time location of a respective cardiac activation.

11. A system for mapping data to a three-dimensional model of an atrial anatomic structure, the system comprising:
a computing device configured to receive complex fractionated atrial electrogram (CFAE) signals, the computing device comprising:
a processor; and
computer-executable instructions that, when executed by the processor, cause the computing device to:
analyze both positive and negative deflections of a CFAE signal over an analysis time period of said signal; and
determine at least one characteristic of said signal based at least in part on analyzing both positive and negative deflections of said signal over said analysis time period by:
determining cardiac activation locations of said signal based at least in part on analyzing both positive and negative deflections of said signal over said analysis time period by:
determining activation location marker candidates; and
for each activation location marker candidate:
determining a maximum peak and a minimum peak;
determining a peak-to-peak voltage as a difference between the maximum peak and the minimum peak; and
eliminating the activation location marker candidate if the peak-to-peak voltage is below a predetermined minimum peak-to-peak voltage threshold; and
determining a complex fractionated electrogram (CFE) mean interval between cardiac activation locations; and
map the at least one characteristic of said signal to the three-dimensional model.

12. The system of claim 11 wherein to determine at least one characteristic, the computer-executable instructions further case the computing device to:
apply a boundary condition criteria to the determination of cardiac activation locations at a beginning and end of said analysis time period of said signal; and
recalculate the CFE mean between cardiac activation locations of said signal over said analysis time period following application of the boundary condition criteria.

13. The system of claim 11 wherein the plurality of cardiac activation location markers are further determined at least in part by analyzing first and second derivatives of both positive and negative deflections of said signal over said analysis time period of said signal.

14. A computer implemented method for mapping an anatomic structure, the computer implemented method comprising:
- generating a three-dimensional computer model of the anatomic structure;
- positioning an electrode carrier in proximity to the anatomic structure with the electrode carrier having a plurality of electrodes thereon;
- generating an electrogram signal from said electrodes;
- determining at least one characteristic of the anatomic structure based at least in part on positive deflections and negative deflections of the electrogram signal, wherein determining at least one characteristic comprises:
  - determining time locations of a plurality of cardiac activations over an analysis time period of the electrogram signal;
  - determining a mean time between successive time locations of the plurality of cardiac activations;
  - applying a boundary condition criteria to the determination of time locations of the plurality of cardiac activations at a beginning and end of the analysis time period of the electrogram signal; and
  - recalculating the mean time between successive time locations of the plurality of cardiac activations following application of the boundary condition criteria; and
- associating the determined at least one characteristic with the three-dimensional computer model of the anatomic structure.

15. The computer implemented method of claim 14 wherein determining at least one characteristic of the anatomic structure is conducted irrespective of the orientation of the electrode carrier relative to the anatomic structure.

16. The computer implemented method of claim 14 wherein the electrogram signal is a complex fractionated atrial electrogram (CFAE) signal.

17. The computer implemented method of claim 16 wherein determining a mean time comprises determining a complex fractionated electrogram (CFE) mean between cardiac activation locations of the CFAE signal.

18. The computer implemented method of claim 17 wherein associating the determined at least one characteristic comprises mapping the CFE mean to the three-dimensional computer model.

* * * * *